(12) United States Patent
Singh et al.

(10) Patent No.: US 8,133,676 B2
(45) Date of Patent: Mar. 13, 2012

(54) GENETIC PROCESS FOR MULTIPLEX TERMINAL RESTRICTION FRAGMENT LENGTH POLYMORPHISM ANALYSIS

(75) Inventors: Brajesh Singh, Aberdeen (GB); Colin Campbell, Aberdeen (GB)

(73) Assignee: The James Hutton Institute, Dundee (GB)

( * ) Notice: Subject to any disclaimer, the term of this patent is extended or adjusted under 35 U.S.C. 154(b) by 229 days.

(21) Appl. No.: 11/640,066

(22) Filed: Dec. 15, 2006

(65) Prior Publication Data

US 2007/0141614 A1 Jun. 21, 2007

(30) Foreign Application Priority Data

Dec. 15, 2005 (GB) .................................. 0525523.7

(51) Int. Cl.
*C12P 19/34* (2006.01)

(52) U.S. Cl. ...................................................... 435/6.12

(58) Field of Classification Search ........................ None
See application file for complete search history.

(56) References Cited

U.S. PATENT DOCUMENTS

| | | | | |
|---|---|---|---|---|
| 5,858,692 | A | 1/1999 | Friedman et al. | 435/7.93 |
| 6,613,520 | B2 | 9/2003 | Ashby | 435/6 |
| 2004/0132095 | A1 | 7/2004 | Iizumi et al. | 435/7.1 |
| 2004/0241662 | A1 | 12/2004 | Robey et al. | 435/6 |
| 2005/0037408 | A1* | 2/2005 | Christensen et al. | 435/6 |
| 2005/0112601 | A1* | 5/2005 | Hassibi et al. | 435/6 |
| 2005/0233360 | A1* | 10/2005 | Davies et al. | 435/6 |
| 2006/0172330 | A1* | 8/2006 | Osborn et al. | 435/6 |

OTHER PUBLICATIONS

Avaniss-Aghajani et al. Molecular Technique for Rapid Identification of Mycobacteria. Journal of Clinical Microbiology 34(1), Jan. 1996, p. 98-102.*
Yu et al. Quantitative Molecular Assay for Fingerprinting Microbial Communities of Wastewater and Estrogen-Degrading Consortia. Appl. Env. Micro. 71(3):1433-1444, Mar. 2005.*
Inagaki et al. Molecular phylogenetic analyses of reversetranscribed bacterial rRNA obtained from deep-sea cold seep sediments. Env. Micro. 4(5):277-286 (2002).*
Rudi et al. Explorative Multivariate Analyses of 16S rRNA Gene Data from Microbial Communities in Modified-Atmosphere-Packed Salmon and Coalfish. Appl. Env. Micro. 70(8):5010-5018, Aug. 2004.*

(Continued)

*Primary Examiner* — Samuel Woolwine
(74) *Attorney, Agent, or Firm* — Drinker Biddle & Reath LLP

(57) ABSTRACT

There is provided a method of nucleic acid analysis which allows analysis of genetic diversity in multiple populations to be performed rapidly and simultaneously. The method comprises (a) isolating nucleic acid from said sample; (b) providing at least two pairs of labelled primers, wherein each said primer pair is complementary to a marker sequence in a nucleic acid of at least one member; (c) amplifying the nucleic acid; (d) digesting the labelled amplified nucleic acid with at least one restriction enzyme to produce restriction fragments, and size sorting said fragments to produce a restriction fragment length profile, and (e) analysing said restriction fragment length profile so obtained; wherein the primer pairs provided for each marker have a different sequence to the sequence of the primer pairs for each other marker, and wherein each said primer pair is uniquely labelled relative to the other primer pair(s). In one embodiment each primer pair is uniquely labelled at the 5' end with a fluorophore. The restriction fragments can be conveniently analysed by a DNA sequencer. The method of the invention has the advantage that it allows nucleic acid amplified using multiple marker sequences to be simultaneously analysed.

14 Claims, 5 Drawing Sheets

OTHER PUBLICATIONS

Figure 1:
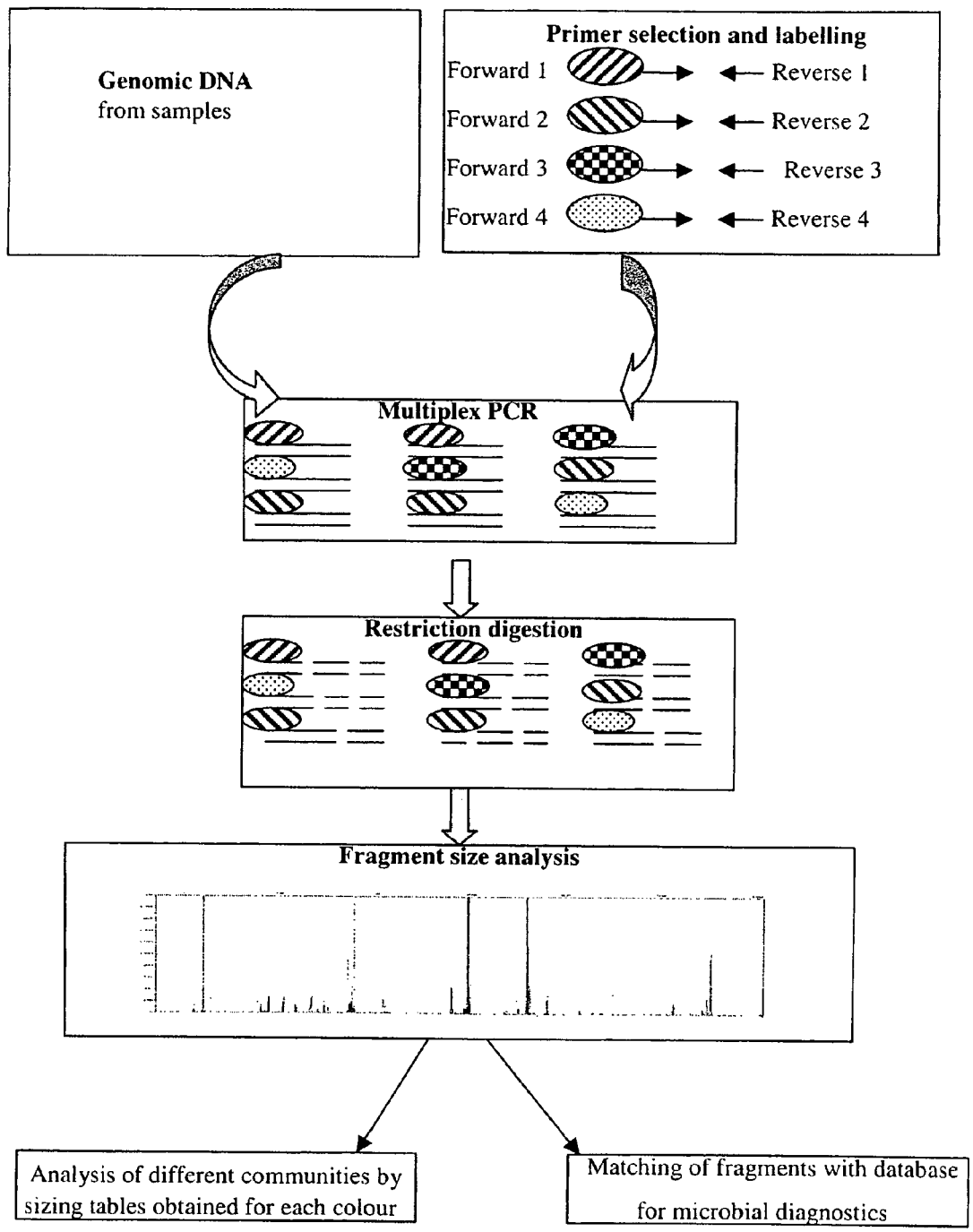

Edwards et al. Multiplex PCR: Advantages, Development, and Applications. PCR Methods Appl 3:65-75 (1994).*

Anderson et al., "Molecular differentiation of metastriate tick immatures", *Vector Borne and Zoonotic Diseases* 4(4): 334-342, 2004.

Gonzalez et al., "Differential diagnosis of *Taenia saginata* and *Taenia saginata* asiatica taeniasis through PCR", *Diagnostic Microbiology and Infectious Disease* 49(3): 183-188, 2004.

Lyons et al., "Screening for bacterial-fungal associations in a southeastern US salt marsh using pre-established fungal monocultures", *FEMS Microbiology Ecology*, 54(2): 179-187, 2005.

Ferrero et al., "Preliminary characterization of microbial communities in high altitude wetlands of northwestern Argentina by determining terminal restriction fragment length polymorphisms", *Revista Latinoamericana de Microbiologia* 46 (3-4): 72-80, 2004.

Smith et al., "T-align, a web-based tool for comparison of multiple terminal restriction fragment length polymorphism profiles", *FEMS Microbiology Ecology* 54(3): 375-380, 2005.

Marsh et al., "Terminal restriction fragment length polymorphism analysis program, a web-based research tool for microbial community analysis", *Applied and Environmental Microbiology*, 66(8): 3616-3620, 2000.

Singh et al., "Use of multiplex terminal restriction fragment length polymorphism for rapid and simultaneous analysis of different components of the soil microbial community", *Applied and Environmental Microbiology* 72(11): 7278-7285, 2006.

Singh et al., "Multiplex-terminal restriction fragment length polymorphism", *Nature Protocols* 1(5): 2428-2433, 2006.

Christensen et al., "Rapid Identification of Bacteria from Positive Blood Cultures by Terminal Restriction Fragment Length Polymorphism Profile Analysis of the 16S rRNA Gene", *Journal of Clinical Microbiology* 41(8): 3790-3800, 2003.

Osborn et al., "An evaluation of terminal-restriction fragment length polymorphism (T-RFLP) analysis for the study of microbial community structure and dynamics", *Environmental Microbiology* 2(1): 39-50, 2000.

* cited by examiner

```
SEQUENCE LISTING

<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: Primer 63F

<400> SEQUENCE: 1
aggcctaaca catgcaagtc                                              20

<210> SEQ ID NO 2
<211> LENGTH: 20
<212> TYPE: DNA
<213> ORGANISM: Artificial
<220> FEATURE:
<223> OTHER INFORMATION: Primer 1087R

<400> SEQUENCE: 2
ctcgttgcgg gacttaaccc                                              20

<210> SEQ ID NO 3
<211> LENGTH: 22
<212> TYPE: DNA
<213> ORGANISM: Artificial
<220> FEATURE:
<223> OTHER INFORMATION: Primer ITS 1F

<400> SEQUENCE: 3
cttggtcatt tagaggaagt aa                                           22

<210> SEQ ID NO 4
<211> LENGTH: 20
<212> TYPE: DNA
<213> ORGANISM: Artificial
<220> FEATURE:
<223> OTHER INFORMATION: Primer ITS 4R

<400> SEQUENCE: 4
tcctccgctt attgatatgc                                              20

<210> SEQ ID NO 5
<211> LENGTH: 20
<212> TYPE: DNA
<213> ORGANISM: Artificial
<220> FEATURE:
<223> OTHER INFORMATION: Primer Ar3F

<400> SEQUENCE: 5
ttccggttga tcctgccgga                                              20

<210> SEQ ID NO 6
<211> LENGTH: 18
<212> TYPE: DNA
<213> ORGANISM: Artificial
```

```
<220> FEATURE:
<223> OTHER INFORMATION: Primer AR927R

<400> SEQUENCE: 6
cccgccaatt cctttaag                                                 18

<210> SEQ ID NO 7
<211> LENGTH: 20
<212> TYPE: DNA
<213> ORGANISM: Artificial
<220> FEATURE:
<223> OTHER INFORMATION: Primer 8F

<400> SEQUENCE: 7
agagtttgat cctggctcag                                               20

<210> SEQ ID NO 8
<211> LENGTH: 19
<212> TYPE: DNA
<213> ORGANISM: Artificial
<220> FEATURE:
<223> OTHER INFORMATION: Primer 1492R

<400> SEQUENCE: 8
ggttaccttg ttacgactt                                                19

<210> SEQ ID NO 9
<211> LENGTH: 20
<212> TYPE: DNA
<213> ORGANISM: Artificial
<220> FEATURE:
<223> OTHER INFORMATION: Primer AmpF

<400> SEQUENCE: 9
ggtcctccga tcgttgtcag                                               20

<210> SEQ ID NO 10
<211> LENGTH: 20
<212> TYPE: DNA
<213> ORGANISM: Artificial
<220> FEATURE:
<223> OTHER INFORMATION: Primer AmpR

<400> SEQUENCE: 10
cgacgagtgg gttacatcga                                               20

<210> SEQ ID NO 11
<211> LENGTH: 18
<212> TYPE: DNA
<213> ORGANISM: Artificial
<220> FEATURE:
<223> OTHER INFORMATION: Primer Rhiz-1244r

<400> SEQUENCE: 11
ctcgctgccc actgtcac                                                 18
```

GENETIC PROCESS FOR MULTIPLEX TERMINAL RESTRICTION FRAGMENT LENGTH POLYMORPHISM ANALYSIS

The present invention concerns a method of nucleic acid analysis. Specifically, the present invention concerns a method for performing rapid and simultaneous analysis of genetic diversity in multiple populations.

A number of techniques are available for nucleic acid analysis. Examples include denaturing gradient gel electrophoresis (DGGE), amplified ribosomal intergenic spacer analysis (RISA), single strand conformation polymorphion (SSCP), amplified rRNA restriction analysis (ARDRA), cloning and sequencing, and terminal restriction fragment length polymorphism (TRFLP).

Terminal restriction fragment length polymorphism (TR-FLP) is a technique generally used to determine the diversity of genes in a selected community of organisms. In this technique, the target gene is amplified using the polymerase chain reaction (PCR) using a 5' fluorescently tagged primer. The amplification products are then digested with at least one restriction enzyme to give different length fragments.

In principle each fragment represents a unique genome in the sample. Genetic diversity will affect the position of cleavage due to the specificity of the restriction enzyme, giving rise to a unique fragment pattern for each genetic population present.

The fragments are then placed onto an automated sequencer. The sequencer is able to detect and measure the fluorescently labelled fragments, and since the length of these fragments is unique to each genome type present in the population or community, the results provide information on the number of populations present in the sample and their relative proportion (see Osborn et al; Environmental Microbiology 2.1 (2000):39-50; Marsh et al., Current Opinion in Microbiology 2.3 (1999): 323-327; Blackwood, Applied and Environmental Microbiology 69:2 (2003):926-32). TRFLP is frequently used in analysing microbial communities. Thus, for example, Nunan et al. (Applied and Environmental Microbiology 71 (2005):6784-6792) report the use of TRFLP and DGGE in the analysis of soil bacterial communities.

However, like other fingerprinting methods, TRFLP has the disadvantage that only one community type (eg. a single taxa of bacteria, fungi, archaea etc) can be analysed at a time. Thus, communities involving more than one taxa need multiple TRFLP procedures using individual taxon-specific primers to be conducted and this is both time consuming and expensive.

TRFLP and multiplex PCR (see Song et al., FEMS Microbiol Lett 187 (2000):167-173 and Veiga et al., Mol Cell Probes 20 (2006):100-104) have been used separately for microbial diagnostics. However, both approaches have been criticised for specific limitations. For example, multiplex-PCR has been mainly used for the detection of specific microbial strains. In such a scenario, a laboratory is expected to have prior knowledge of the likely microbial contaminants and then use primers specific to the target microorganism(s) in multiplex-PCR. The conventional TRFLP method has been criticised for the lack of resolution. One terminal restriction fragment (TRF) can represent more than one bacterial species (see Avaniss-Aghajani et al., J. Clin Microbiol 34 (1996):98-102). For higher resolution, it is required to use different primer sets digested with different enzymes (Christensen et al., J. Clin Microbiol 41 (2003):3790-3800). This approach is time consuming and expensive.

There is thus a need for a technique which allows simultaneous analysis of a multiple-taxa and functions (functional gene diversity) in a simple and cost-effective manner.

WO 04/024944 describes a technique involving multiple amplifications of target nucleic acid sequences which can be used to detect, identify and quantify a complex mix of bacteria in water.

Clinical and regulatory agencies often require environmental samples, food products and clinical samples to be tested for multiple organisms. For example, food products are commonly tested for *Salmonella* spp. *E. coli, Clostridium perfringens, Listeria monocytogenes* amongst other micro-organisms.

We have now found a rapid and sensitive method able to analyse communities comprising two or more taxa at the same time. In contrast to other protocols, the method of the present invention provides data on multiple communities or multiple target genes in just one reaction, thereby saving time, cost and labour.

The present invention thus provides a method of genotyping two or more members in a sample comprising a population of micro-organisms, said method comprising:
 a) isolating nucleic acid from said sample;
 b) providing at least two pairs of labelled primers, wherein each said primer pair is complementary to a marker sequence in a nucleic acid of at least one member;
 c) amplifying the nucleic acid;
 d) digesting the labelled amplified nucleic acid with at least one restriction enzyme to produce restriction fragments, and size sorting said fragments to produce a restriction fragment length profile, and
 e) analysing said restriction fragment length profile so obtained,
wherein the primer pairs provided for each marker have a different sequence to the sequence of the primer pairs for each other marker, and wherein each said primer pair is uniquely labelled relative to the other primer pair(s).

A schematic diagram showing the method of the present invention is shown in FIG. 1.

The method of the present invention relies on detection of terminal fragments of PCR amplified target DNA by a DNA sequencer. To detect terminal restriction fragments (TRFs), primers specific to different taxa or genes are labelled at the 5' end with a unique fluorescent dye. After the restriction digestion of the PCR products, TRFs are detected by a DNA sequencer (see FIG. 1).

Generally the population of micro-organisms will comprise two or more members, for example, may have 3, 4, 5, 6, 7, 8 or more different members present. Each member can be a different taxa, or may be a different function (enzymic ability, antibiotic resistance etc.) present in the population. The member may thus be a micro-organism or property of the population.

The nucleic acid present in the sample provided can represent, for example, a diverse population of bacterial species or a combination of bacterial, fungi or other micro-organism species.

The step of amplifying the nucleic acid can be conducted by any suitable technique. Most of the DNA amplification techniques rely on enzymic methods in which a DNA polymerase catalyses the reaction. Best known is the polymerase chain reaction (PCR) method (see U.S. Pat. No. 4,683,195, U.S. Pat. No. 4,483,202 and U.S. Pat. No. 4,800,159 for details). Also suitable is the reverse transcription—PCR, which is a combination of PCR and a reverse transcription reaction (see Trends in Biotechnology 10:146-152 (1992)) which enables amplification from DNA or RNA.

These methods rely upon a three-step process involving:
i) denaturing double-stranded DNA into a single stranded form;
ii) annealing a primer to the single stranded DNA; and
iii) synthesising or extended the complementary strand from the primer.

In the present invention the primer annealed to the single stranded DNA is the labelled primer provided in step b).

Optionally the step of annealing the primer and extending the primer are conducted at the same temperature (Shuttle PCR; see Protein, Nucleic Acid and Enzyme, Supplement 41 (5):425-428, 1996).

Other alternative methods include the ligase chain reaction (LCR) method (see EP 320308) and the transcription based amplification system (TAS) method (see PCR Protocols, Academic Press, Inc (1990) pages 245-252).

In the present invention, the primers will be taxa-specific for each marker to be analysed. The marker can be representative of a population present in the sample or can indicate a functional ability within the sample (eg. an enzymic function, antibiotic resistance or the like).

The primers will be of any suitable length to facilitate nucleic acid amplification, whilst enabling a suitable degree of specificity for the member concerned. Thus, the primer will usually be of 12-20 nucleotides, but this length is not critical.

Conveniently the primers selected should have similar melting temperatures, for example have a melting temperature within 10° C. of each other, preferably within 5° C. of each other, for example within 2 to 3° C. of each other, to enable the amplification step to be conducted in a single process. Primers of dissimilar melting temperatures could however be accommodated using separate PCT protocols.

Exemplary primers for microbial analysis (including of ampicillin resistant *E. coli*) are set out below in Table 1. Other suitable primers are well known in the art and could also be used. Many suitable primers are available or can be produced commercially (eg. from Applied Biosystems, Invitrogen or the like) or are described in published literature.

phores include LIZ, VIC, FAM and HEX, PET, NED, Cy3 Cy5 and any other fluorophores which are used for detection by a sequencer, or which could be so used. Generally the fluorophores will be distinguishable from each other to enable identification.

In one embodiment the method of the present invention is used in combination with Quantative polymerase chain reaction (Q-PCR) in conjunction with reverse transcription. An alternative technique is real time polymerase chain reaction (RT-PCR).

As mentioned above, restriction fragment length analysis can be conducted automatically or semi-automatically using a nucleotide sequencer. One of the advantages of the present invention is that nucleic acid amplified using multiple marker sequences can be simultaneously analysed. Suitable equipment includes DNA sequencers from the Applied Biosystem Instruments, Beckman Coulter or all other suppliers.

Any suitable restriction enzyme can be used in the method of the invention. Generally, however, a restriction enzyme selected for use in the method of the invention recognises and cleaves a nucleic acid at a specific target sequence. Usually the target sequence will comprise at least 3 or 4 nucleotides. Ideally, the target sequence will be present in the nucleic acid being analysed and its position will vary depending on the specific allele present. The selection of suitable restriction enzymes is already well-known from the prior art methods of RFLP and TRFLP and the same selection criteria apply here also. Thus, there is a significant knowledge of suitable restriction enzymes in the art, and the majority of such enzymes are available commercially.

Notwithstanding the significant prior art knowledge and information available on suitable restriction enzymes, the following non-limiting, list of enzymes can be used in the present invention:

Hae III, Hha, I, Msp I, Rsa I, Taq I, and other commercially available restriction enzymes.

Optionally more than one restriction enzyme may be used to produce the restriction fragments. For example, 2, 3, 4 or 5

TABLE 1

Exemplary list of primers for microbial analysis

| Name | Fluorescent dye | Sequence (5' to 3') | SEQ ID No | Target region | Specificity |
|---|---|---|---|---|---|
| For community analysis | | | | | |
| 63F | None | agg cct aac aca tgc aag tc | 1 | 16S rRNA gene | Eubacteria |
| 1087R | IC (green) | ctc gtt gcg gga ctt aac cc | 2 | 16S rRNA gene | Eubacteria |
| ITS 1F | FAM (blue) | ctt ggt cat tta gag gaa gta a | 3 | ITS | All fungi |
| ITS 4 | None | tcc tcc gct tat tga tat gc | 4 | ITS | All fungi |
| Ar3F | None | ttc cgg ttg atc ctg ccg ga | 5 | 16S rRNA gene | All archaea |
| AR927R | NED (yellow) | ccc gcc aat tcc ttt aag | 6 | 16S rRNA gene | All archaea |
| For microbial diagnostic study | | | | | |
| 8F | NED (yellow) | aga gtt tga tcc tgg ctc ag | 7 | 16S rRNA gene | Eubacteria |
| 63 F | FAM (blue) | agg cct aac aca tgc aag tc | 1 | 16S rRNA gene | Eubacteria |
| 1492R | VIC (green) | ggt tac ctt gtt acg act t | 8 | 16S rRNA gene | Eubacteria |
| AmpF | NED (yellow) | ggt cct ccg atc gtt gtc ag | 9 | β-lactamase gene | Ampicillin resistant gene |
| AmpR | None | cga cga gtg ggt tac atc ga | 10 | β-lactamase gene | Ampicillin resistant gene |

The primers will be labelled, usually at the 5' end. Fluorophores are suitable labels since this allows automation of measurement of the restriction fragment length.

In one embodiment of the multi-taxa TRFLP method of the present invention (herein "M-TRFLP"), the primers provided to each marker sequence will be uniquely labelled relative to the primers provided to each other marker. Suitable fluororestriction enzymes may be used in the digestion stage. For the purpose of the present invention, all that is required is that each amplified nucleic acid is digested by at least one restriction enzyme.

In one embodiment of the present invention the sample containing amplified nucleic acid is divided into two or more portions, and each portion is subjected to a restriction enzyme digestion, with at least one restriction enzyme. Optionally different restriction enzymes (or different combinations of restriction enzymes) can be used for each portion or subdivision of the sample.

The method of the present invention can be used to analyse, identify and/or relatively quantify micro-organisms or other complex mixtures of nucleic acid in any situation. For example, the method of the present invention can be used to analyse microbial fauna in soil for monitoring, environmental or research purposes. In particular it is envisaged that the method of the present invention will be particularly suitable for environmental monitoring of land and water. Alternatively, the method of the present invention can be used to identify or monitor the micro-organism populations (and their functional potential) in food products, drinks (eg milk), animal foodstuffs, pharmaceuticals, grain or other biodegradable products (such as paper). Further, the micro-organism population in a hospital or other medical grade building can be analysed or monitored using the method of the present invention. Likewise, this method can be used to simultaneously identify micro-organisms causing infection in a patient, their pathogenic genes and the multiple antibiotic resistance genes of such micro-organisms, in a single procedure. The method of the present invention can be used in agriculture, forestry, bioremediation, environmental analyses, ecology, clinical microbiology, forensic science, medicine, geochemical exploration, food, pharmaceutical and other industries where microbial processes or detection is required.

For microbial diagnostics, the M-TRFLP can be used in two formats if required, (1) it can be used for detection of any microbial contaminants in food or industrial products. For this format, universal bacterial primers for selected DNA targets such as 16s rRNA gene, ITS, DNA gyrase gene etc can be used. If required, more than one set of primers can be used for one or more target DNA sequences. The profiles from different DNA targets can be distinguished from one another by labelling the different primers with unique fluorescent dyes. Hence, in one reaction step detection of any microbial contaminant and its identity can be achieved. (2) M-TRFLP can also be used for simultaneous detection of a pathogen and its pathogenic capabilities. For example, if a sample needs to be screened for the presence of *Clostridium botulinum* and identification of a strain type is needed, the primer sets specific for universal structural gene (16S rDNA and ITS) of bacteria can be used along with primers for *botulinum* neurotoxin (BoNT) genes specific to the bacterial species. This approach will confirm presence or absence of any microbial contaminant including *Clostridrium* species. If *Clostridium* presence is detected, it will also confirm whether the strain is capable of producing specific toxins. A similar approach can be used for the detection of other microbial strains. Using a combination of universal and group specific primers may also help in detecting microbes which are found in low abundance.

Similarly, M-TRFLP can be used in two formats for community analysis also. In one format, only structural diversity of the different communities (such as bacterial, fungal, archaeal etc) can be targeted. In a second format, M-TRFLP can be used for analysis of structural and functional communities of the samples. For example, M-TRFLP can be used for simultaneous analysis of bacterial, fungal diversity along with nitrifying and denitrifying communities in one reaction step.

This method can be further improved by combining with quantitative-PCR for quantitative information (see Yu et al., Appl Environ Microbiol 71 (2005):1433-1444) and can be combined with other methods such as amplification of ancient DNA for more utility (see Rompler et al., Nature Protocol 1 (2006):720-728).

Thus, the present invention provides a method of analysing micro-organism taxa or function within a sample, said method comprising:

a) isolating nucleic acid from said sample;

b) providing at least two pairs of labelled primers, wherein each said primer pair is complementary to a marker sequence in a nucleic acid of at least one micro-organism;

c) amplifying the nucleic acid;

d) digesting the labelled amplified nucleic acid population with at least one restriction enzyme to produce restriction fragments, and size sorting said fragments to produce a restriction fragment length profile; and e) analysing said restriction fragment length profile so obtained, wherein the primer pairs provided for each marker have a different sequence to the sequence of the primer pairs for each other marker, and wherein each primer pair is uniquely labelled relative to the other primer pair(s).

In one embodiment the sample will be a blood or urine sample or other tissue specimen and the method will be used for simultaneous analysis to identify pathogens, pathogenic genes and the antibiotic resistance of bacteria present in that sample.

The present invention also envisages the creation of databases to enable easy identification of a member, in respect of the organism its functional capabilities and genetic traits.

The present invention will now be described in more detail with reference to the following, non-limiting, examples and figures, in which:

FIG. 1 is a schematic outline of the procedure for use of M-TRFLP in a microbial diagnostic process.

FIG. 2 is a community profile obtained for archaeal, bacterial and fungal communities by the method of the invention (M-TRFLP) and individual TRFLP for a single sample. The first panel contains profile generated from the method of the invention (M-TRFLP) for bacterial, fungal and archaeal communities together using multiplex-PCR. The second panel (TRFLP-Bacteria) is the TRFLP profile generated for the same sample from PCR products using only eubacterial specific primers. The third and fourth panels are TRFLP profile obtained for fungal and archaeal communities in the same sample using fungal and archaeal specific primers in separate PCR reaction.

FIG. 3 shows the bacterial community profile generated by three different approaches of TRFLP (A). The first panel shows the bacterial community profile in one sample in the method of the invention (M-TRFLP) generated from multiplexed PCR. The second panel shows the TRFLP profiles generated from pooled PCR products from individual PCRs. The third panel shows TRFLP profile for bacterial community of the same sample obtained from individual PCR from using eubacterial specific primers. For comparison, all other dyes except LIZ (marker) and VIC (dye linked to bacterial primer) were switched off for panel 1 and 2 before capturing pictures. Part B of this figure shows the comparison of profiles for fungal communities of the same sample generated by three TRFLP approaches. The panels are arranged in same order as for bacterial profiles. Here, for panel 1 and 2, only LIZ and FAM (dye linked to fungal primer) channel were kept switch on to help comparing profiles obtained from the different TRFLP approaches.

Figure 4:
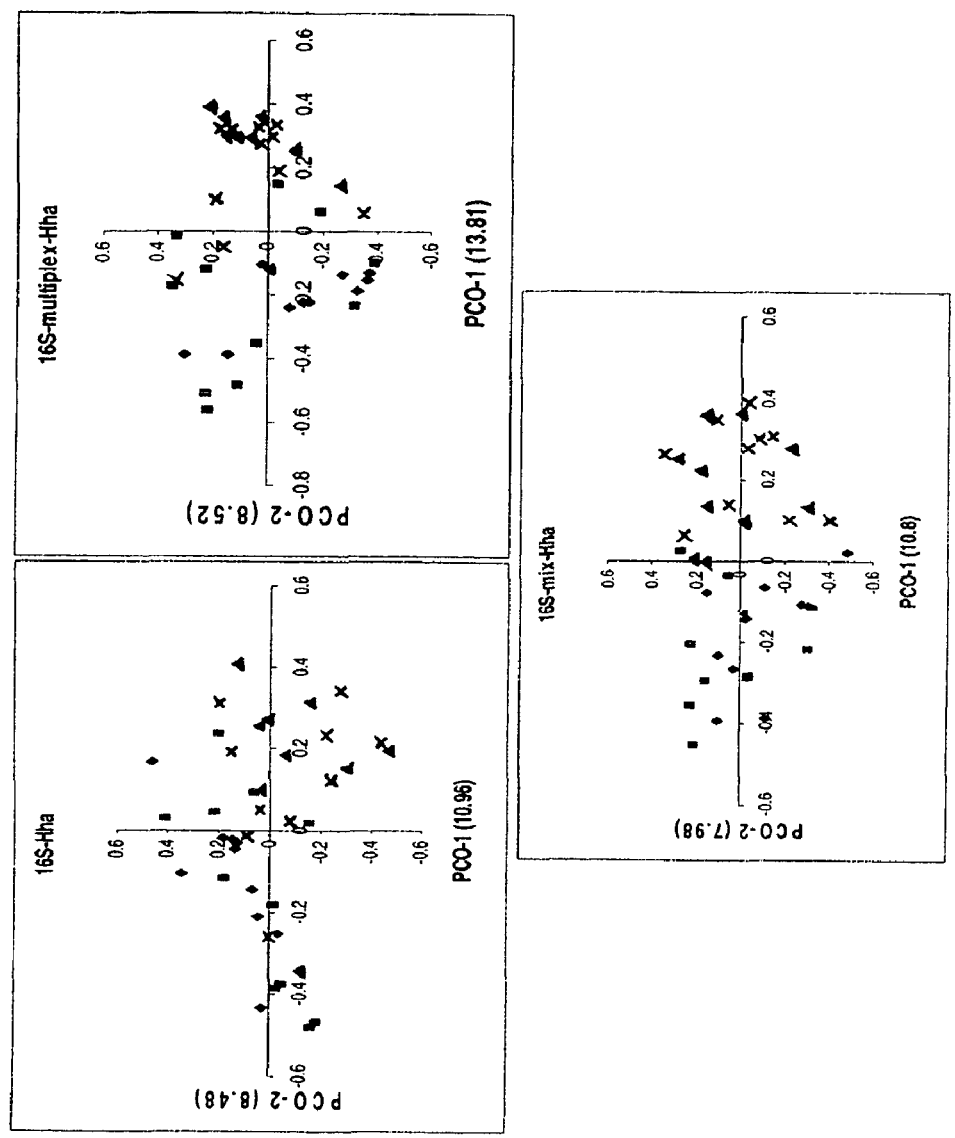

FIG. 4 gives the PCO analysis for bacterial community obtained from three different TRFLP approaches for 43 soil samples from Abernethy forest. The percentage values in the bracket on the X and Y axis represent the amount of variation accounted for each axis.

Figure 5:
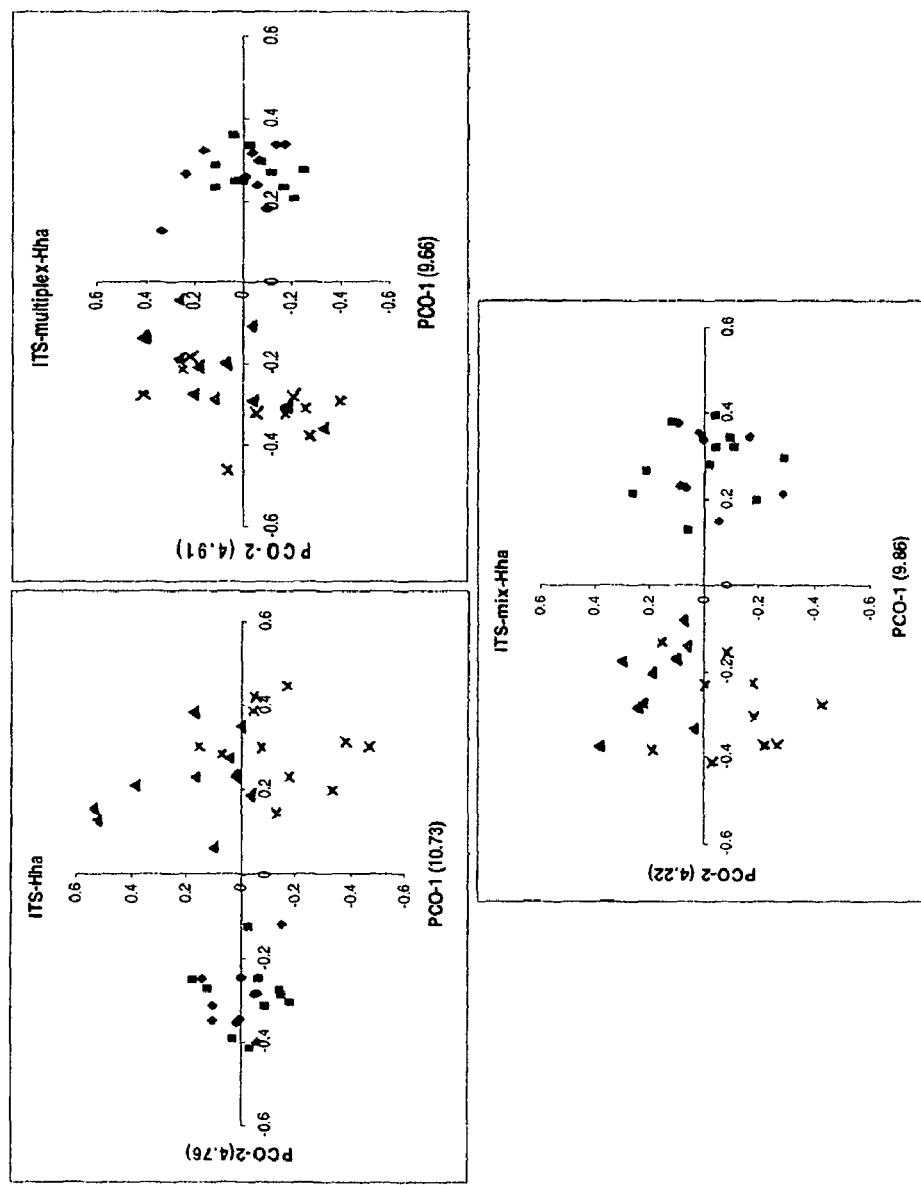

FIG. 5 gives the PCO analysis for fungal community obtained from three different TRFLP approaches for 43 soil samples from Abernethy forest region. The percentage values in the brackets on X and Y axis represent the amount of variation accounted for each axis.

EXAMPLES

Example 1
Experimental Procedure

Development of M-TRFLP

A summary of the rationale for the method of the invention (M-TRFLP) is presented in FIG. 1.

The preliminary development work on the M-TRFLP method used 6 soil samples obtained from a pot experiment. The soils from a grassland site (Cairnbrogie, National Grid ref: NJ848 266, 10.2% organic matter), were planted with *Lolium perenne* for a period of months prior to sampling. Samples were collected from the rhizospheres of the rye grass.

DNA was extracted from each soil sample using the Ultra-Clean™ Soil DNA Isolation Kit according to the manufacturer's instructions.

PCR Conditions and Optimisation

DNA samples were amplified with PCR primers (Table 2) specific to bacteria, fungi and archaea individually. Following this, a multiplex PCR reaction was performed for each DNA sample containing all three primer pairs for fungi, bacteria and archaea. All PCR reactions were performed using the same conditions. The PCR master mix (50 µl) contained 1× $NH_4$ reaction buffer, 2 mM $MgCl_2$, 250 µM of each dNTP, 2.5 units of Biotaq DNA polymerase (all reagents from Bioline, London, UK), 20 µg BSA (Roche Diagnostic, Lewes, UK) and 2 µl of template DNA. Initially, 10 pmol of each primer was used for both individual and multiplex PCR but amplification of fungal ITS regions in multiplex PCR was poor (data not shown). Therefore, the concentration of fungal ITS primers was doubled to 20 pmol for all further PCR amplifications. Both individual and multiplex PCR reactions were performed with a DYAD™ DNA Engine® Peltier Thermal Cycler (MJ Research, Waltham, Mass., USA) using the same program. The program consisted of an initial step of 5 minutes at 95° C. followed by 30 cycles including a denaturing step at 95° C. for 30 s, an annealing step at 55° C. for 30 s and an elongation step at 72° C. for 1 min. The last cycle was followed by a final extension at 72° C. for 10 min. PCR amplicons were visualised on a 1% agarose gel under UV radiation.

TABLE 2

| Primer Name | Fluorescent Label | Sequence from 5' to 3' | Target gene | Specificity |
|---|---|---|---|---|
| 63f | None | AGGCCTAACACATGCAAGTC SEQ ID No. 1 | 16S rRNA | Eubacteria |
| 1087r | VIC (green) | CTCGTTGCGGGACTTAACCC SEQ ID No. 2 | 16S rRNA | Eubacteria |
| Ar3f | None | TTCCGGTTGATCCTGCCGGA SEQ ID No. 3 | 16S rRNA | Archaea |
| AR927R | NED (yellow) | CCCGCCAATTCCTTTAAG SEQ ID No. 6 | 16S rRNA | Archaea |
| ITS1f | FAM (blue) | CTTGGTCATTTAGAGGAAGTAA SEQ ID No. 3 | ITS gene | All Fungi |
| ITS4r | None | TCCTCCGCTTATTGATATGC SEQ ID No. 4 | ITS gene | All Fungi |
| Rhiz-1244r | PET (red) | CTC GCT GCC CAC TGT CAC SEQ ID No. 5 | 16S rRNA | Rhizobia/ agrobacteria |

T-RFLP Analysis

PCR products were purified using the GenElute™ PCR clean-up Kit (Sigma-Aldrich, Dorset, UK) according to the manufacturer's instructions. Prior to digestion, purified PCR product concentrations were determined on a spectrophotometer (UV photometer, Eppendorf, Germany). All PCR products obtained from individual taxa and multiplex PCR were digested with Hae III, Hha I, Msp I or Rsa I restriction enzymes. The PCR products were digested separately with different enzymes in a 20 µl reaction mixture containing 500 ng of PCR products, 1× buffer, 0.1 µg·µl$^{-1}$ of acetylated BSA and 20 units of restriction enzyme (all reagents from Promega). Samples were incubated at 37° C. for 3 hours followed by an inactivation step at 95° C. for 15 min. Two different T-RFLP analyses were performed per DNA sample. T-RFLP profiles were produced for amplicons generated with the primers for bacteria, fungi and archaea individually, as well as in a multiplex PCR reaction containing all primer pairs. After digestion, 2 µl of each sample was mixed with 0.3 µl of LIZ-labelled 500 internal size standard and 12 µl of formamide (all reagents from Applied Biosystems, Warrington, UK). Prior to fragment analysis, samples were denaturated at 95° C. for 5 min and then chilled on ice for 5 min. Fragment size analysis was carried out on an ABI PRISM® 3130x/Genetic Analyzer (Applied Biosystems, Warrington, UK).

Data Analysis

T-RFLP profiles were produced using GeneMapper (version 3.7) software. T-RFs were quantified using the advanced mode and second order algorithm. Only peaks between 50 and 500 bp were considered to avoid T-RFs caused by primer-dimers and to obtain fragments within the linear range of the internal size standard. The relative abundance of a particular T-RF within a T-RFLP profile was calculated as the respective peak height divided by the total peak height of all T-RF's in a profile. All peaks with a height less than 0.5% of the total peak fluorescence was excluded from further analysis. This approach minimises the effect of variations in the TRFLP profiles caused by the quantity of DNA analysed. A peak by peak comparison was carried out between T-RFLP profiles produced from the same sample using individual taxa PCR and multiplex PCR products of the three taxa. T-RFLP profiles (electropherograms) obtained using the two approaches were aligned against each other and compared as were the tables of peaks generated by GeneMapper (version 3.7) software. Similarity matrices for the two approaches were calculated for the profile of bacteria, fungi and archaea for each individual DNA sample by comparing the TRFLP data generated using individual and multiplex PCR products. This was expressed in percentage by dividing the number of peaks present in both profiles divided by the total number of peaks present in one profile with lower number of peaks.

Application of M-TRFLP

Field Site and Sampling

Rhizosphere soil samples of *Calluna vulgaris* and *Vaccinium vitis-idaea* were collected from a naturally regenerating Scots pine (*Pinus sylvestris*) forest at Abernethy, Cairngorm, Scotland (National Grid Reference NJ027122 (Chapman et al., Soil Biology & Biochemistry 35:6 (2003): 753-764) which extends onto open moorland. The area between the open moor and the forest has been partially colonised by Scots pine trees and is termed the transition zone. The colonising trees are approximately 15-20 years old. Few seedlings exceed 1-1.3 m in height (see Chapman et al., supra). Samples were taken along three parallel transects, one each in the forest (F), transition (T) and moorland (M) regions. Each transect was X m long and divided into 10 sections with 11 points in total, X m apart. A *Calluna vulgaris* plant and associated rhizosphere soil was collected from each point along the three transects. In addition, a *Vaccinium vitis-idaea* plant was also collected from each point along the forest transect. Rhizosphere/rhizoplane soil samples were taken from all (44) plants collected (Nunan et al., Applied and Environmental Microbiology 71:11 (2005) 6784-6792). DNA was extracted from all 44 samples as described above but only 43 samples produced good quality DNA for PCR and were used in the analysis.

M-TRFLP Analysis of Field Samples

M-TRFLP analysis was conducted as described above except that the microbial taxa investigated were bacteria, fungi and rhizobia. Rhizobia/agobacteria were chosen in place of archaea to see if the presence of individual genera which would be expected to low in number in this habitat could be detected using this approach. Initially, five randomly selected samples were chosen to test the efficacy and reliability of the approach given that the complement of primers to be used in the multiplex PCR reaction was different. As before, T-RFLP profiles were produced for PCR products generated for bacteria, fungi and rhizobia individually and for products generated using multiplex PCR containing all three primer pairs. Additionally for this experiment, the amplicons produced by using the primers for bacteria, fungi and rhizobia/agrobacteria individually were pooled in a 2:2:1 ratio for each soil sample and were subjected to fragment analysis. These samples were first digested with four restriction enzymes namely; Hae III, Hha I, Msp I and Rsa I. The enzymes Hha I and Msp I produced more peaks with a more even distribution and higher consistency. Optimisation of DNA quantity for restriction digestion was carried out with three different DNA concentrations (1000, 500 and 200 ng) in 20 µl reaction mix. Samples with 500 ng DNA gave the best result. Therefore, all subsequent restriction digestions were carried out with HhaI and MspI with 500 ng of DNA except the individual rhizobial PCR product for which 200 ng DNA was used.

Later, all 43 soil DNA samples were amplified with three primer sets (for 16S, ITS and RHIZ individually and mixed together (multi-taxa PCR) which gave 172 PCR products. The fragment size analysis was performed using all three approaches described above. In the first approach, the PCR products from individual PCR (i.e. with each individual primer set for 16S and ITS or RHIZ) were digested with restriction enzyme Hha I and Msp I separately giving 258 samples for T-RFLP. The second approach for the T-RFLP experiment consisted of pooling together PCR products from each individual PCR and performing the digestion with both enzymes separately to give 86 T-RFLP analyses. Finally, for the third approach, all 43 samples from the multiplex PCR were digested separately with both enzymes, which gave another 86 samples for fragment size analysis. After digestion, profiles for individual and M-TRFLP were generated as before.

The data were analysed as before but the presence or absence of predicted peaks found using the rhizobial primers and enzymes were also compared to the Microbial Community Analysis III (MiCA III) database (http://mica.ibest.uidaho.edu/trflp.php).

Statistical Analysis

Fragment data obtained from T-RFLP and M-TRFLP analysis were exported to Excel (Microsoft, Redmond, Wash.) and converted into binary data (presence or absence of individual peaks). A principal co-ordinate (PCO) analysis was then performed on the binary data using GenStat (8$^{th}$ edition, VSN International Ltd, Hempstead, UK) to identify any underlying patterns in the data. PCO analysis was carried out separately on the data obtained for the three different approaches to test the consistency of method. PCO analysis was chosen because the Jaccard similarity matrix is appropriate for binary data where the absence of a peak in both samples is less indicative of similarity than the presence of a peak in both samples.

Results

Development and Validation of M-TRFLP from Glasshouse Experiments

Figure 2:
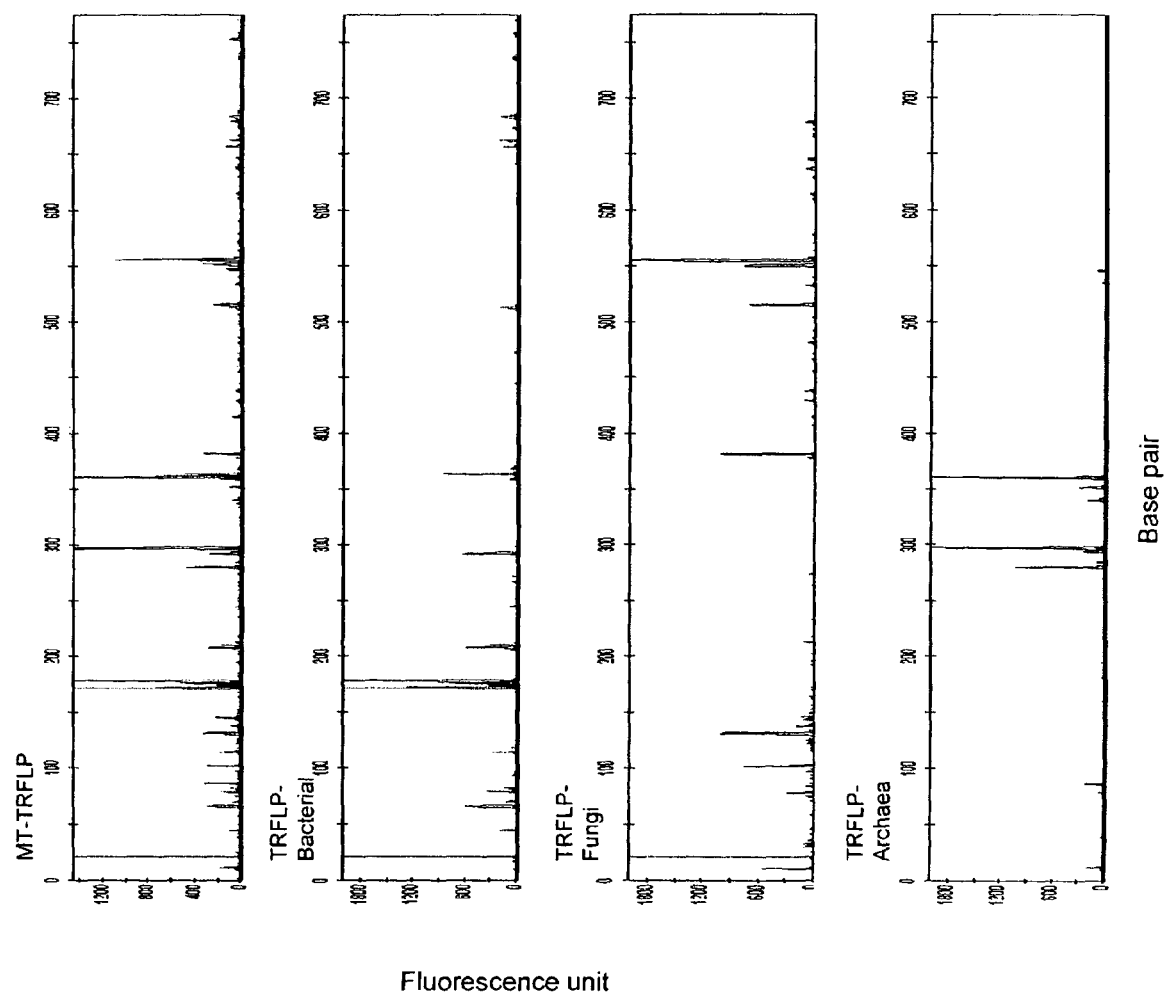

As expected, amplicons of various sizes were obtained for each of the 6 soil DNA samples amplified with mixed primers. Profiles generated by the two different approaches, single taxa and M-TRFLP, produced identical profiles (FIG. 2) for each taxon primer pair. Similarities between profiles were not only observed in terms of the presence and absence of peaks but also in terms of the relative dominance of particular peaks for any single taxon. Most of the samples analysed by single TRFLP and M-TRFLP were >90% similar to each other for all taxa. High similarities were obtained (Table 3) between individual and M-TRFLP in terms of presence and absence of the peaks for each taxon for all samples digested with all restriction enzymes.

TABLE 3

Similarity matrix for individual and M-TRFLP obtained for six sample digested with HhaI.

| | Archaea | Bacteria | Fungi |
|---|---|---|---|
| 1 | 100% | 92% | 88% |
| 2 | 100% | 91% | 91% |
| 3 | 100% | 92% | 93% |
| 4 | 88% | 96% | 92% |
| 5 | 86% | 90% | 93% |
| 6 | 86% | 95% | 96% |

Between, 6-10 peaks were produced using the for archaeal primes in all 6 soils. Peak by peak comparison for archaeal community suggested that both TRFLP approaches produced identical profiles. A comparatively lower percentage similarity (>86%) between the single and multi-taxa approaches for samples 4, 5 and 6 was obtained. This was in part due to the fact that one peak (fragment number) was below the threshold value of selection (<0.5% relative to total peak fluorescence intensity). For bacterial communities, 20-31 peaks were taken for comparison on the basis of their relative intensity of more than 0.5% of the total fluorescence of the profile. Again the % similarity was high (>90%; Table 3). Manual comparison of data again revealed that little differences between the two profiles generated by two approaches for the same sample. Differences again occurred due mainly to, 1-3 peaks in one profile fell below 0.5% of total fluorescence. The highest number of fragments was observed for fungal communities with between 24-49 fragments observed in the different samples. As with the archaeal and bacterial communities the similarity of the two TRFLP approaches was high (>88%) and the minor differences observed in the profile was again caused by the threshold used in the data analysis. Further analysis of the data generated by GeneMapper software using lower threshold gave even higher similarities between the two different approaches for all three taxa.

M-TRFLP Analysis of Field Soils

Figure 3:
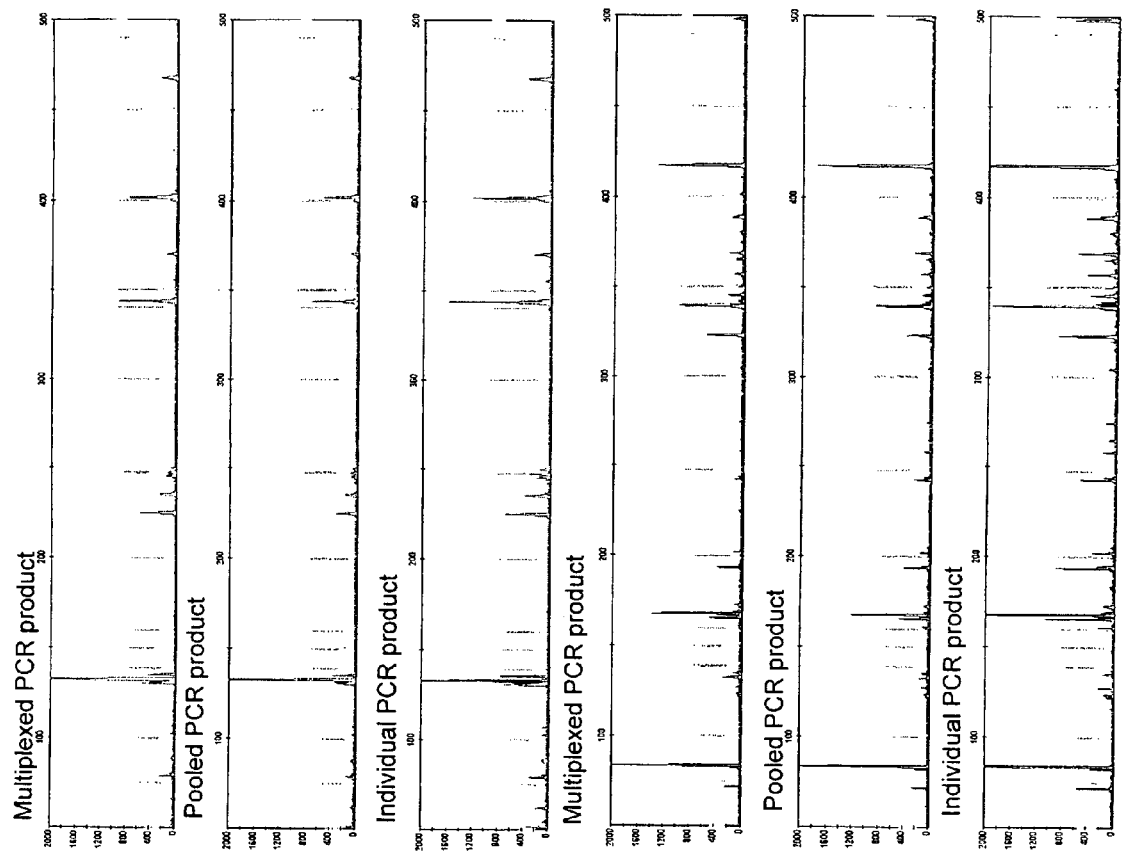

For this experiment, three different set of data were generated for each sample; (1) TRFLP profiles generated by normal PCR with individual taxon (bacterial, fungal and rhizobial) specific primers (2) TRFLP profiles generate for all three taxa after PCR with individual taxon-specific primers and then pooling of PCR products in the reaction tube before restriction digestion and subsequent fragment size analysis, and (3) M-TRFLP profiles generated after multiplex PCR. Here too, when the data was analysed for bacterial, fungal and rhizobial communities, the profiles generated for the same samples by either TRFLP analysis of individual or pooled PCR products, or multiplex PCR were consistent with each other (FIG. 3). Peak by peak comparison for each microbial taxon gave a very high percentage similarity. Again the raw data gave near identical peak profiles for the two approaches of TRFLP, obtained for the same taxon of a given sample, but in data processed to remove minor peaks (Table 3) there were a few differences. However, all dominants peaks were present in both profiles of TRFLP and M-TRFLP.

The database search on the MiCA III web site predicted the presence of only two TRFs for rhizobia/agrobacteria when digested with HhaI (153 and 154 bp) and one TRF when digested with MspI (90 bp) for the primer combination used in this study. However, in our samples, two TRFs of 156 and 158 bp were detected in samples digested with HhaI. The signal intensity for these two TRFs was significantly reduced in the M-TRFLP analysis compared to the TRFs generated from samples amplified with the individual rhizobia primers or the pooled PCR products. Samples digested with MspI, produced two TRFs of 86 and 88 bp in size in both individual and M-TRFLP instead of the one peak of 90 bp predicted from virtual analysis performed on the MiCA III website. The similarity of TRFLP profiles obtained for rhizobia was comparatively smaller (85%) than for the other taxa when comparing the two techniques. However, when the raw data was analysed with a reduced cut off value for the signal intensity, the TRFs were detected in all samples. However, in addition to the predicted TRFs, there were also additional peaks detected in several samples however, these were inconsistent across the samples and were of relatively very low signal intensity.

In a later experiment, to increase the level of rhizobia fluorescence intensity, we amplified a few of these samples with different set of primers (for multiplex PCR) where the reverse eubacterial primers used was 1492R instead of 1087R and the other primers were as described before. This approach lead to several fold increase in the fluorescence intensity of rhizobia peaks in M-TRFLP. Further increase in the rhizobial fluorescence in M-TRFLP was observed when both primers were rhizobial specific.

Principal Coordinate Analysis of Data of Field Samples

Data obtained using the three T-RFLP approaches (individual PCR, pooled PCR products, and multiplex PCR) were analysed separately and compared with each other for both the bacterial and fungal communities for the two enzymes used. FIG. 4 shows the clustering of samples according to the PCO scores of dimension one and two. These PCO scores were obtained from the analysis of bacterial 16S rRNA genes digested with the enzyme Hha I. Results from the PCO analysis of the 16S marker digested with the enzyme Hha I showed that the first three dimensions of PCO accounted for only 27% of the variability. The ordination of the data showed the samples from the forest (FV and FC) could be discriminated from the samples from the moorland and transition zones (MC and TC). This pattern was consistent for all three T-RFLP approaches.

Results obtained from the PCO analysis of the fungal ITS sequences digested with the enzyme Hha I were similar to the bacterial 16S data but with a stronger clustering according to the habitat types where all the samples from the forest, irrespective of the plant type, were clustered together. Similarly, the samples from the moorland and the transition habitats were clustered together. This pattern was consistent in the individual and the M-TRFLP. Similar results were also obtained for bacterial and fungal communities when the samples were digested with MspI (data not shown).

Discussion

The examples describe the use of TRF profiling for the multi-taxa analysis of microbial communities, and validates the method of the invention for the simultaneous analysis of several taxa of microbial communities in one reaction by using structural gene specific PCR primers, restriction digestion and sizing of the TRFs. The results confirm that M-TRFLP is a rapid, highly reproducible and consistent as TRFLP but is comparatively cheaper and less labour intensive method for the analysis of microbial communities where information on more than one taxa is required or desirable. Use of TRFLP as an approach to identify bacterial pathogens from blood cultures was taken before (Christensen et al., Journal of Clinical Microbiology 41.8 (2003):3790-3800). They obtained TRF profiles for each organism by sizing fragments from two sets of 16S rDNA specific fluorescently labelled primers (FAM and Hex) and was digested with various restriction enzymes. However, our approach has additional ability to analyse more than one taxa by incorporating different dyes to primers specific to individual taxon. The method described here could be very appropriate for and easily adapted to other biotic interactions such as protozoa-microbial interaction, nematode-microbial interactions where directly comparable predator prey relations needed to be understood. The method will have wide application in environmental health monitoring where information on more than one taxa will be required. Other application includes monitoring of bio-control agents and their targets as well as the survival of mixed bioremedial communities and their impact on native micro-flora. This approach and methods can also be used to study functional diversity (diversity of functional genes) along with structural diversity in a more convenient and economical way and may help in assigning a particular function to non-cultivable microbes in soil by linking presence of particular functional gene with presence of specific microorganisms.

TRFLP is one of the most widely used methods for the analysis of microbial communities since its first evaluation for soil samples (Osborne et al., Environmental Microbiology 2.1 (2000):39-50. It has proved to be more consistent and reproducible fingerprinting methods than others because of its automated analysis mode. It provides semi-quantitative data which can be used for information on relative abundance of the operational taxonomic unit (Blackwood et al., Applied and Environmental Microbiology 69.2 (2003):926:932); Marsh, Current Opinion in Microbiology 2.3 (1999):323-327).

M-TRFLP is a major advancement in molecular analysis which allow simultaneous characterisation of up to four taxa in one reaction mix (sequencer allows simultaneous detection of up to four florescent dyes). This is unique in the sense that no other fingerprinting method can do this at the present time and is likely to be a very useful intermediate approach between the single taxa and the phylogenetic microarray methods.

In the examples, the only minor PCR optimisation that was required was to double the amount of fungal primer concentration in comparison with bacterial primers which probably reflects the comparative size of different taxa genome. Profiles produced for the same sample by individual TRFLP and M-TRFLP were almost identical with high similarities (>90%). Whatever differences were observed that was mainly caused by the mode of data analysis The loss of small peaks is well documented in TRFLP analysis but can be optimised if necessary by lowering the fluorescence threshold or by manual correction (Osborn et al., Environmental Microbiology 2.1 (2000):39-50). When we compared raw data without this analysis, peak by peak comparison gave almost 100% similarities. We took this approach of data analysis because it is well established method to avoid very small peaks which may have appeared as artefacts (Blackwood et al., supra). Other reasons may be a minor shift in position of few peaks during the electrophoresis of the samples. For example, if a specific peak has a base pair size of 100.45 in one sample and 100.54 in other samples, conversion into whole number for further analysis will give peak size of 100 and 101 even though they are same. We did not take this variation into the account. Even so, the high similarity of profiles between individual TRFLP and M-TRFLP shows the robustness of this new method. When three individual taxa PCR products were pooled before restriction digestion, the resulting profiles were almost identical to those obtained from individual and M-TRFLP for corresponding samples. This approach was taken to investigate if there is a variation between individual and M-TRFLP profiles, at what stage this variation is caused i.e. during PCR or restriction digestion and fragment size analysis. Our results confirmed that at least in this experiment, it was not essential to use individual PCR when conducting M-TRFLP. Consequently, this saves considerably on time and costs.

It is known that the greater discrimination in profiles can be provided by labelling the forward primer because of length heterogeneities at the 5' end of the gene (Osborn et al., supra). To take this fact into account, we also tested other approaches where forward bacterial primer and reverse fungal primers or only forward primers for both bacterial and fungal communities were labelled to investigate the impact on the profiles of the communities. These approaches showed no effect on the robustness of the method and the data were consistent and reproducible (data not shown).

In the initial experiment, although detectable, the peak heights for the rhizobial TRFs were very small. In subsequent analysis we successfully increased the peak size by using different primer sets. In the initial experiment we used 63F and 1087R primers for eubacterial and 63F (same used for eubacterial) and 1244R for rhizobial community for M-TRFLP. However in the subsequent experiment, we increased the peak height several fold by using the 63F and 1494R instead of 1087R for the eubacterial community in the multiplex PCR. This might be explained by the fact that in the first experiment, rhizobial specific primer products of first cycle had binding sites for both eubacterial and rhizobial reverse primers which led to competition between eubacterial (1087R) and rhizobial (1224R) primers in the second and subsequent cycles. This is supported by the observation that an even further increase in the peak height and intensity was obtained when the samples were amplified for M-TRFLP using both forward and reverse rhizobia specific primers. Thus complementarity of primers should be taken into account during the selection of primer sets for M-TRFLP and probably for the best results, both primers used should be specific to a given taxon.

The principal coordinate analysis of the data generated by individual and M-TRFLP for each taxon confirmed both methods had similar results (FIG. 4). The bacterial communities in the samples were discriminated according to habitats types with the bacterial communities clustered together irrespective of plant species in the soil from the forest and similarly the moorland and transitions soils were also closely clustered together. A similar pattern was obtained for the fungal communities with even tighter clustering for habitat types. Similar results were obtained for the same site before for the fungal community using DGGE (Anderson et al., Environmental Microbiology 5.11 (2003):1121-1132). Several previous studies have found similar results where habitats or soil types have stronger impact on microbial communities than the individual plant species (Alvey et al., Biology and Fertility of Soils 37.2 (2003):73-82; Bossio et al., Microbial Ecology 36.1 (1998):1-12; Brodie, et al., Microbial Ecology 44.3 (2002) 260-270; Girvan et al., Applied and Environmental Microbiology 70.5 (2004):2692-2701; Marschner et al., Soil Biology and Biochemistry 33.11 (2001):1437-1445). Again a slight difference between PCO plots generated from individual and M-TRFLP can be attributed to method of identifying peaks. However, overall trends of results were almost identical emphasising the reproducibility of the new method. The better discrimination of the fungal method is in part due to the greater resolution afforded by using ITS primers. Combining the data for the different taxa gives even better discrimination of habitat type. Clearly this can be done by combining the raw data for each single taxon analysis but using M-TRFLP is more economical with no apparent loss of information.

In conclusion, multi-taxa TRFLP is a new way of obtaining greater detail and resolution of the microbial community structure in a more economic fashion. The innovation in combining the primers for different taxa is potentially valuable if coupled with rational primer selection to examine specific biotic interactions between different populations and species. This study reports the development and validation of a new method; M-TRFLP for the first time, that permits the simultaneous analysis of more than one taxa. This method is highly reproducible and can be used for the study of a range of biotic interactions. This method provides all features of normal TRFLP and therefore can be used for semi-quantitative information on all taxon analysed. This method can also be used for analysis of functional diversity and interactions between structural and functional diversity which are being explored at this moment. The number of taxa or primers is limited by the available dyes and filter technologies to four dyes. This limit is inherent due to the need to determine the four nucleotides comprising DNA and RNA and there is a possibility that the number of dyes and so different tax/functions could be increased further by chemical and engineering modifications to existing sequencer machines.

Example 2

Materials

Reagents
Taq polymerase (Bioline, London, UK),
PCR buffer (Bioline, London, UK),
dNTP (Bioline, London, UK),
Bovine serum albumin (BSA) (Roche Diagnostic Limited, East Sussex, UK)
Sterile water (Promega, Southampton, UK)
Primers for multiplex-PCR (Applied Biosystem Instruments, Warrington, UK).
Standard size marker (Applied Biosystem Instruments, Warrington, UK)
Deionised formamide (Applied Biosystem Instruments, Warrington, UK)
Running buffer and EDTA (Applied Biosystem Instruments, Warrington, UK)
Ethanol (VER International, Lutterworth, UK)
Sodium acetate trihydrate (Sigma-Aldrich, Poole, UK)
Nuclease free water (Promega, Southampton, UK)
Glacial acetic acid (Sigma-Aldrich, Poole, UK).
Restriction enzymes (Promega, Southampton, UK)
Appropriate buffer (Promega, Southampton, UK)
Acetylated BSA (Promega, Southampton, UK)
Sterile water (Promega, Southampton, UK)
Equipment
PCR machine (DYAD™ DNA Engine® Peltier Thermal Cycler, MJ Research,
DNA sequencer, (Applied Biosystem Instruments, UK)
Centrifuge (Beckman Coulter, UK)
Reagent Setup
3 mM Sodium Acetate: Add 50 mls dH$_2$O to 40.824 g sodium acetate, mix and heat. Adjust pH to 4.6 with glacial acetic acid, make up the volume to 100 ml. The solution should be autoclaved before use.
Procedure
Multiplex-PCR.

1) Select target primers where each set is labelled with a unique fluorescent dye at its 5' end. All primers should have similar melting temperatures.
2) Mix all PCR reagents in the following concentration for community analysis. The PCR master mix (50 μl) should contain 1×PCR buffer, 2 mM MgCl$_2$, 250 μM of each dNTP, 2.5 units of DNA polymerase, 20 μg Bovine Serum Albumin and 2 μl of template DNA. Concentrations of all reagents can be adjusted for optimal amplification depending on the quality of template DNA and target genes. Primer concentration can also be adjusted on the basis of the specificity and number of target gene copy.
3) Perform multiplex PCR on a thermocycler using a programmed consisting of an initial step of 5 minutes at 95° C. followed by 30 cycles, including a denaturing step at 95° C. for 30 s, an annealing step at 50° C.-65° C. (depending on the melting temperature of the primers) for 30 s and an elongation step at 72° C. for 1 min. The last cycle should be followed by a final extension at 72° C. for 10 min.
4) Stain PCR amplicons with ethidium bromide (0.1 mg/ml) and visualise on a 1% agarose gel under UV radiation. Different size amplicons for different primer sets, this should be visible on the agarose gel.
Cleaning up of PCR Products
5) Various commercial kits are supplied by life science companies. To keep cost low, ethanol precipitation of the PCR products can be used.
Typical Procedure for Ethanol Precipitation
a) Add ethanol (100 μl for a tube; 25 ml for a 96 well plate).
b) Add sodium acetate (5 μl for a tube; 1.25 ml for a 96 well plate).
c) Mix. If using a 96 well plate, dispense 100 μl per well.
d) Incubate at −20° C. for at least 20 minutes.
  PAUSEPOINT: The −20° C. incubation can be left overnight, if preferred.
e) Spin at maximum speed in a centrifuge for 10-30 min (14,100 g for a tube; 1109 g for a 96 well plate).
f) Remove supernatant. Use a pipette for the tube, taking care not to disturb the pellet. For a 96 well plate, place the plate upside down gently over a filter paper towel.
g) Add 150 μl 70% ethanol per tube or well.
h) Incubate at −20° C. for 10 minutes.
i) Spin at maximum speed in a centrifuge for 10-30 min (14,100 g for a tube; 1109 g for a 96 well plate).
j) Remove supernatant. Use a pipette for the tube, taking care not to disturb the pellet. For a 96 well plate, place the plate upside down gently over a filter paper towel.
k) For a tube, air dry in a dessicator. For a 96 well plate, place the plate over a fresh filter paper towel and pulse spin briefly (about 30 s) upside down. Check the pellet is still inside the well.
l) Dissolve the pellet in 10-20 μl nuclease free water.
Restriction Digestion
6) Use the purified PCR products as substrates for restriction enzymes. The selection of restriction enzymes depends on the heterogeneity of the target sequence. For microbial 16S rDNA, several public databases are available on line such as MiCA (http://mica.ibest.uidaho.edu/digest.php) and RDPII (http://rdp.cme.msu.edu), for selecting suitable enzymes for specific primer sets. For other genes, the available sequences can be retrieved from the public databases such as EMBL or NCBI which can be aligned to predict the size of TRFs for a particular combination of primers and restriction enzyme. We use HaeIII (GG^CC), HhaI (GCG^C), MspI (C^CGG) and RsaI (GT^AC) restriction enzymes independently for the digestion of PCR products in a 20 μl reaction mixture containing 500 ng (for community analysis) and 50 to 200 ng (for microbial diagnostics) of PCR products. Also include 1× buffer, 0.1 μg μl$^{-1}$ of acetylated BSA and 20 units of restriction enzyme.

7) Incubate samples at 37° C. for at least 15 min followed by a deactivation step at 95° C. for 10 min. Please note some restriction enzymes (such as TaqI) have optimum activity at 65° C.

Fragment Size Analysis.

8) Determine the lengths of the TRF by electrophoresis on a sequencer. After digestion, transfer 1 μl of the restricted PCR product to a MicroAmp optical 96-well reaction plate and mix with 0.3 μl of LIZ-labelled GeneScan™-500 internal size standard and 12 μl of Hi-Di™ (highly deionised) formamide. Various other size markers (with different colour and base pair size) are available from the suppliers. The Liz labelled GeneScan™-500 Standard gives peaks at 35, 50, 75, 100, 139, 150, 160, 200, 250, 300, 340, 350, 400, 450, 490 and 500 bp (FIG. 1).

9) Prior to fragment analysis, denature samples at 95° C. for 5 minutes and chill on ice for 5 minutes.

10) Load the fluorescently labelled DNA into the capillaries and separate the DNA fragments according to their size. Use running buffer 1× Genetic Analyser Buffer with EDTA (1 mM EDTA [pH 8.0] for capillary electrophoresis. Use the running conditions listed in Table 4 for the sequencer. Other sequencer manufacturers supply their own size standards and running buffers but that will not interfere with data quality.

TABLE 4

Running condition of the ABI PRISM ® 3130xl for the analysis of the TRFLP fragments.

| | |
|---|---|
| Oven temperature | 60° C. |
| Injection voltage | 1.6 kVolts |
| Injection time | 15 seconds |
| Running voltage | 15 kVolts |
| Running time | 2,500 seconds |
| Column | capillaries 16 × 50 μm × 50 cm |
| Filter set | G5 dye set (FAM, VIC, NED, PET, LIZ) |

Data Analysis.

11) Obtain TRFLP profiles using software attached with the sequencer. In our case, we used GeneMapper (ABI, version 3.7) software. Quantify TRFs using the advanced mode and second order algorithm (other methods can also be used, please see ABI manual for GeneMapper). For community analysis only peaks between 50 and 500 bp are considered because most TRFs fall in this range and to avoid TRFs caused by primer-dimers and to obtain fragments within the linear range of the internal size standard. However, if necessary, peak size larger than 500 bp can also be obtained. For community analysis, the relative abundance data along with the binary (presence/absence) data are important. GeneMapper and other softwares produce table which includes TRF size (in base pair), height and area. Height and area of a particular TRF is directly proportional to the TRF copy number present in the sample, which is used for obtaining the relative abundance of TRFs. The relative abundance of a particular TRF within a TRFLP profile is calculated as the peak height (or area) of that TRF divided by the total peak height (or area) of all TRFs in the profile. All peaks with a height or area of less than 0.5 to 1% of the total peak fluorescence can be excluded from further analysis. This approach minimises the effect of variations in the TRFLP profiles caused by the quantity of DNA analysed. For microbial diagnostics, the TRFs obtained for different target genes can be matched within a database (public or laboratory developed) for positive confirmation of the microbial presence. Setting up a bin for base pair size for microbial diagnostic is useful. The bin size allows adjusting the minor shift in TRF size caused due to running conditions of the sequencer and can be determined by running the same samples on to different sequencers. Usually 1-3 base pair bin gives consistent and good results.

Areas of Improvement (1) Multiplex PCR Step.

No or weak amplification of one set of primers in a multiplex-PCR: If the product of the different sets of primers are of different sizes, weak or no amplification of one or more sets of primers can be picked up during the run of the gel for PCR products. However, if the product size of different sets of primers are the same or very near to each other, this cannot be detected until the fragment size analysis. If this occurs, two approaches are available to sort out this problem. (1) Check the melting temperature of all primers used for multiplex-PCR. It is important that all primers have similar melting temperatures or within a narrow range otherwise products for set(s) of primers whose melting temperature is higher or lower than PCR annealing temperature, will have weak or no PCR product. (2) Increase the concentration of primer set(s) which have previously produced weak/limited PCR product because it may also be caused by the specificity of primers as well as the small number of copy of target genes. Increasing the concentration of primers may overcome this problem.

(2) Fluorescent Dye of Primers.

Fluorescent dyes used for labelling 5' of the primers are very important. Each dye has a specific absorbance wavelength. It is important that the different dyes selected for the primer and size standard labelling should have absorbance maxima that do not overlap. It is also important to check the colour filter of the sequencer machine which is used for fragment size analysis. Different filters have been optimised for different sets of fluorescence. Please see sequencer manuals for more detail.

(3) Shift in Position of TRF.

This step is crucial for microbial diagnostics applications of the method. There is always a minor shift in position for the same TRF when run separately. However, GeneMapper (or other software provided by the sequencer manufacturers) has a function to take this fact into account by setting a bin for it. Bin (1-3 base pair if different sequencer machines are used) can be set depending on the multiple runs of the same samples.

(4) Height and Area of the TRFS.

The height and area of each TRF is directly proportional to the number of copies of the target gene (subject to PCR bias). However, TRFs originating from the same organism, having the same copy number of different target genes may have different height and area. This is because of the differential detection sensitivity of the fluorescence emission from different dyes. If needed, this can be adjusted by mixing unlabelled primers with labelled primer (of dye with higher sensitivity) in ratio to adjust with other dyes.

Anticipated Results

M-TRFLP is a fingerprinting method and upon analysis of data by sequencer software produces TRFs of different base pair size and intensity. For community analysis the M-TRFLP produces several TRFs of different colours which are the products of separate sets of primers. The different coloured TRFs can be used together as an environmental community or can be divided into sub-groups such bacteria, fungi, archaea etc before they are used for statistical analysis. For microbial diagnostics, the number of TRFs for each primer set will usually be an indicator of the number of contaminants present in the sample. The base pair size is unique to a particular genome but each TRF produced (especially for a highly conserved gene such as 16SrRNA gene) may represent more than one species. However, the combination of TRFs produced from different sets of primers by M-TRFLP can be used to identify a microbial strain up to species and sub-species level.

The most critical step for M-TRFLP is the choice of primers for multiplex PCR. All primers should have similar melting temperatures. This fact should be taken into consideration during selection of the primers. However, if it is essential to use two sets of primers with different melting temperatures for desirable results, separate PCR can be run on individual set of primers and then the PCR products can be mixed before restriction digestion and fragment size analysis. Just like any other method, appropriate controls for each step should be maintained throughout the experiment. M-TRFLP is a simple, reliable technique for community analysis and microbial diagnostics and can be used with minimum training.

The invention claimed is:

1. A method of analysing genetic diversity of micro-organisms in a sample, wherein said sample comprises two or more member micro-organisms, said method comprising:
   a) isolating nucleic acid from the micro-organisms in said sample wherein the isolated nucleic acid comprises polymorphic gene sequences;
   b) providing at least two pairs of differently labelled primers, wherein a first primer pair with a first label is complementary to a first target sequence and at least a second primer with a second label is complementary to at least a second target sequence, and wherein said first and at least second target sequences are polymorphic gene sequences;
   c) amplifying the nucleic acid in a single multiplex PCR reaction;
   d) digesting the labelled amplified nucleic acid with a mixture of restriction enzymes to produce restriction fragments, and size sorting said fragments to produce a restriction fragment length profile; and e) analysing said restriction fragment length profile so obtained to genotype said two or more member micro-organisms, to allow analysis of the genetic diversity of the micro-organisms in the sample.

2. The method as claimed in claim 1 wherein the sample has three or four different member micro-organisms present.

3. The method as claimed in claim 2 wherein each member of the population is a different taxa.

4. The method as claimed in claim 1 wherein the primers are of 12 to 20 nucleotides in length.

5. The method as claimed in claim 2 wherein all of the primers have similar melting temperatures.

6. The method as claimed in claim 5 wherein all of the primers have a melting temperature within 10° C. of each other.

7. The method as claimed in claim 1 wherein said first or at least second primer pair is labelled with a fluorophore.

8. The method as claimed in claim 1 wherein Q-PCR and reverse transcription are used in step c) to amplify the nucleic acid.

9. The method as claimed in claim 1 wherein the sample containing the amplified nucleic acid is divided into two or more portions and each portion is subjected to restriction enzyme analysis using a mixture of restriction enzymes distinct from that used for the other portion(s).

10. The method of claim 1 wherein said sample is a urine, blood or tissue sample obtained from a patient.

11. The method of claim 1 wherein said sample is soil or water.

12. The method of claim 1 wherein said sample is a foodstuff.

13. The method as claimed in claim 1 wherein said sample is obtained from a surface to monitor the cleanliness thereof.

14. A method of analysing genetic diversity of micro-organisms in a sample wherein said micro-organisms are of more than one micro-organism taxa comprising:
   a) isolating nucleic acid from said micro-organisms of more than one taxa in a sample wherein said isolated nucleic acid comprises polymorphic gene sequences;
   b) providing at least two pairs of differently labelled primers wherein a first primer pair with a first label is complementary to a first target sequence and is specific to an individual taxon and at least a second primer with a second label is complementary to at least a second target sequence and is specific to an individual taxon and wherein said first and at least second target sequences are polymorphic gene sequences;
   c) amplifying the polymorphic gene sequence of each taxon in a single multiplex PCR reaction;
   d) digesting the labelled amplified nucleic acid with a mixture of restriction enzymes to produce restriction fragments, and size sorting said fragments to produce a restriction length profile; and
   e) analysing said restriction fragment length profile so obtained to genotype said two or more micro-organisms of more than one taxa to allow analysis of the genetic diversity of the organisms in the sample.

* * * * *